(12) United States Patent
Garthaffner et al.

(10) Patent No.: US 10,994,086 B2
(45) Date of Patent: May 4, 2021

(54) ELECTRONIC VAPING DEVICE WITH TUBULAR HEATING ELEMENT

(71) Applicant: Altria Client Services LLC, Richmond, VA (US)

(72) Inventors: Travis Martin Garthaffner, Midlothian, VA (US); Charles L. Dendy, Ruther Glen, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 15/636,983

(22) Filed: Jun. 29, 2017

(65) Prior Publication Data

US 2019/0001086 A1 Jan. 3, 2019

(51) Int. Cl.
| | |
|---|---|
| *A61M 15/06* | (2006.01) |
| *A61M 11/04* | (2006.01) |
| *A24F 47/00* | (2020.01) |
| *A24F 40/10* | (2020.01) |
| *A24F 40/46* | (2020.01) |
| *H05B 1/02* | (2006.01) |
| *H05B 3/06* | (2006.01) |

(52) U.S. Cl.
CPC ........... *A61M 15/06* (2013.01); *A24F 47/008* (2013.01); *A61M 11/042* (2014.02); *H05B 1/0227* (2013.01); *H05B 3/06* (2013.01); *A61M 2205/3653* (2013.01); *A61M 2205/587* (2013.01); *A61M 2205/8206* (2013.01); *H05B 2203/014* (2013.01); *H05B 2203/021* (2013.01); *H05B 2203/022* (2013.01)

(58) Field of Classification Search
CPC combination set(s) only.
See application file for complete search history.

(56) References Cited

U.S. PATENT DOCUMENTS

| | | |
|---|---|---|
| 5,530,225 A | 6/1996 | Hajaligol |
| 5,649,554 A | 7/1997 | Sprinkel et al. |
| 5,665,262 A | 9/1997 | Hajaligol et al. |
| 5,708,258 A | 1/1998 | Counts et al. |
| 5,750,964 A | 5/1998 | Counts et al. |
| 5,865,185 A | 2/1999 | Collins et al. |

(Continued)

FOREIGN PATENT DOCUMENTS

| | | |
|---|---|---|
| CN | 106418712 A | 2/2017 |
| CN | 106490686 A | 3/2017 |

(Continued)

OTHER PUBLICATIONS

U.S. Appl. No. 15/154,439, filed May 13, 2016.

(Continued)

*Primary Examiner* — Alex B Efta
(74) *Attorney, Agent, or Firm* — Harness, Dickey & Pierce, P.L.C.

(57) ABSTRACT

A cartridge of an electronic vaping device includes a reservoir configured to store a pre-vapor formulation and a heating element configured to heat the pre-vapor formulation. The heating element includes a metal tube having a first end and a second end. The metal tube defines an opening therethrough. The metal tube includes a sidewall defining at least one spiral channel extending substantially continuously along a portion of the metal tube.

20 Claims, 4 Drawing Sheets

(56) References Cited

U.S. PATENT DOCUMENTS

| | | | |
|---|---|---|---|
| 5,878,752 A | 3/1999 | Adams et al. | |
| 6,026,820 A | 2/2000 | Baggett, Jr. et al. | |
| 6,688,313 B2 | 2/2004 | Wrenn et al. | |
| 9,289,014 B2 | 3/2016 | Tucker et al. | |
| 9,420,829 B2 | 8/2016 | Thorens et al. | |
| 2011/0155153 A1* | 6/2011 | Thorens | H05B 3/58 131/329 |
| 2013/0192623 A1* | 8/2013 | Tucker | H01C 17/00 131/329 |
| 2014/0209105 A1* | 7/2014 | Sears | F22B 1/28 131/328 |
| 2014/0238422 A1 | 8/2014 | Plunkett et al. | |
| 2014/0283855 A1 | 9/2014 | Hawes et al. | |
| 2014/0305454 A1 | 10/2014 | Rinker et al. | |
| 2015/0181937 A1* | 7/2015 | Dubief | A24F 47/008 131/329 |
| 2015/0196058 A1* | 7/2015 | Lord | A24F 47/008 131/329 |
| 2015/0223522 A1* | 8/2015 | Ampolini | A24F 47/008 131/328 |
| 2015/0245659 A1* | 9/2015 | DePiano | A24F 47/008 392/397 |
| 2016/0309785 A1 | 10/2016 | Holtz | |
| 2016/0309786 A1 | 10/2016 | Holtz et al. | |
| 2017/0325502 A1 | 11/2017 | Nelson et al. | |
| 2017/0340011 A1* | 11/2017 | Batista | A24F 40/44 |
| 2018/0027879 A1 | 2/2018 | Gavrielov et al. | |

FOREIGN PATENT DOCUMENTS

| | | |
|---|---|---|
| EP | 3031339 A1 | 6/2016 |
| EP | 3287024 A2 | 2/2018 |
| WO | WO-2013083631 A1 | 6/2013 |
| WO | WO-2014/066730 A1 | 5/2014 |
| WO | WO-2016/108694 A1 | 7/2016 |
| WO | WO-2016123738 A1 | 8/2016 |
| WO | WO-2018024742 A1 | 2/2018 |

OTHER PUBLICATIONS

U.S. Appl. No. 15/224,866, filed Aug. 1, 2016.
International Search Report and Written Opinion for International Application No. PCT/EP2018/067674 dated Oct. 18, 2018.
Written Opinion for corresponding International Application No. PCT/EP2018/067674, dated Jun. 6, 2019.
International Preliminary Report for corresponding Application No. PCT/EP2018/067674, dated Oct. 17, 2019.

* cited by examiner

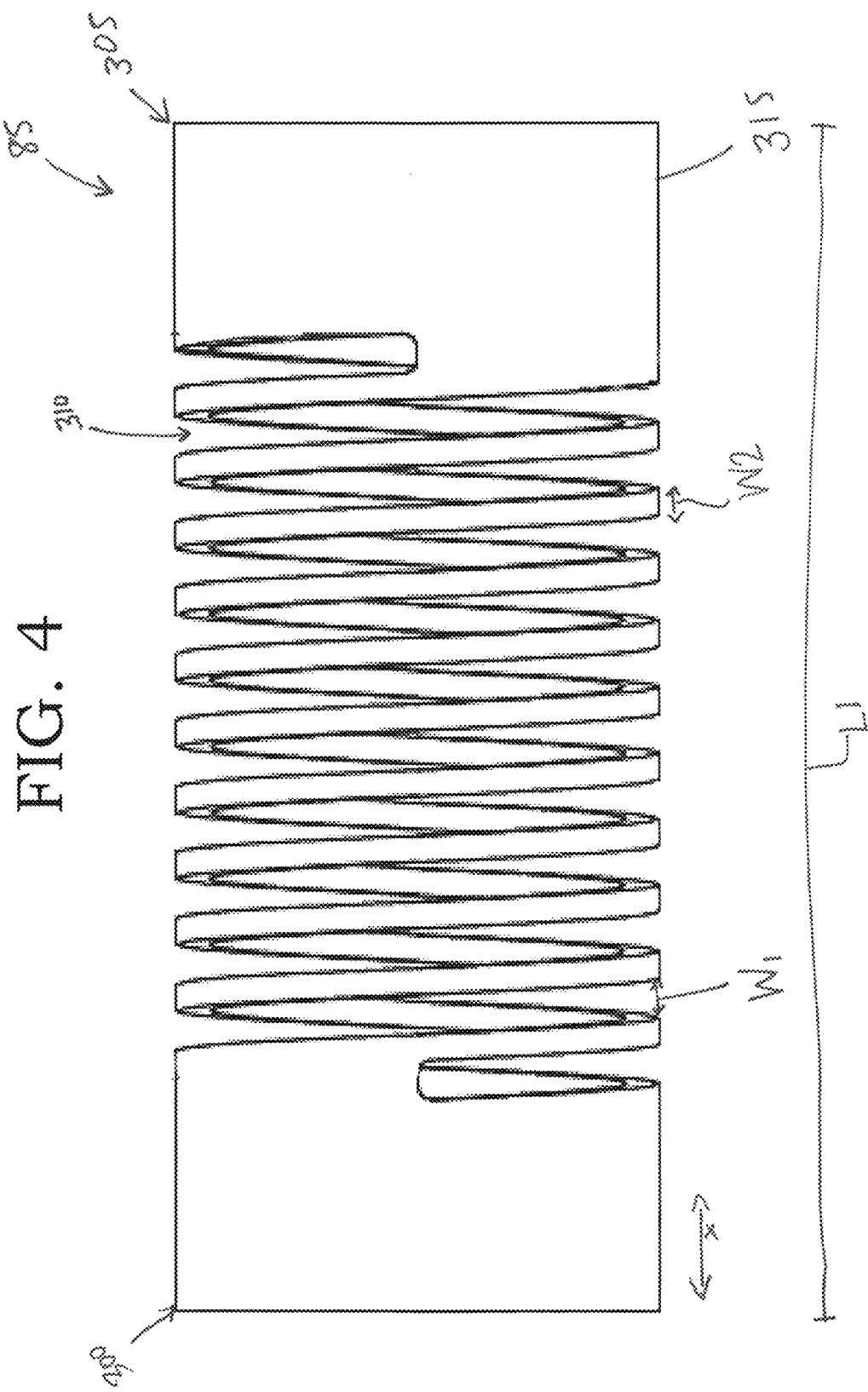

ELECTRONIC VAPING DEVICE WITH TUBULAR HEATING ELEMENT

BACKGROUND

Field

The present disclosure relates to an electronic vaping or e-vaping device.

Description of Related Art

An e-vaping device includes a heating element which vaporizes a pre-vapor formulation to produce a "vapor."

The e-vaping device includes a power supply, such as a rechargeable battery, arranged in the device. The battery is electrically connected to the heating element, such that the heating element heats to a temperature sufficient to convert a pre-vapor formulation to a vapor. The vapor exits the e-vaping device through a mouthpiece including at least one outlet.

SUMMARY

At least one example embodiment relates to a cartridge of an electronic vaping device.

In at least one example embodiment, a cartridge of an electronic vaping device comprises a reservoir configured to store a pre-vapor formulation and a heating element configured to heat the pre-vapor formulation. The heating element includes a metal tube having a first end and a second end. The metal tube defines an opening therethrough. The metal tube includes a sidewall defining at least one spiral channel extending substantially continuously along a portion of the metal tube.

In at least one example embodiment, the spiral channel begins at a location about 0.5 mm to about 1.0 mm from the first end of the metal tube.

In at least one example embodiment, the spiral channel ends at a location about 0.5 mm to about 1.0 mm from at least one of the first end of the metal tube and the second end of the metal tube.

In at least one example embodiment, the spiral channel includes about 2 to about 20 turns around a circumference of the metal tube. Each turn is spaced from adjacent turns by about 0.05 mm to about 0.25 mm. Each turn is uniformly spaced from adjacent turns. In some example embodiments, each turn is non-uniformly spaced from adjacent turns.

In at least one example embodiment, the spiral channel has a width ranging from about 0.1 mm to about 0.5 mm. The metal tube has a length ranging from about 3.0 mm to about 6.0 mm.

In at least one example embodiment, the spiral channel extends along about 2.0 mm to about 3.5 mm of a length of the metal tube. About 0.75 mm to about 2.0 mm of the length of the metal tube does not include the spiral channel.

In at least one example embodiment, the metal tube has an inner diameter ranging from about 0.1 mm to about 4.0 mm. The metal tube has a thickness ranging from about 0.05 mm to about 0.25 mm.

In at least one example embodiment, the cartridge further comprises a wick that extends through the opening in the metal tube, such that the metal tube surrounds at least a portion of the wick.

In at least one example embodiment, the cartridge further comprises a wick that at least partially surrounds at least a portion of the metal tube.

In at least one example embodiment, the heating element has a resistance ranging from about 2.5 ohms to about 4.5 ohms.

In at least one example embodiment, the metal tube is formed of at least one of stainless steel and Nichrome.

At least one example embodiment relates to an electronic vaping device.

In at least one example embodiment, an electronic vaping device comprises a reservoir configured to store a pre-vapor formulation, a heating element configured to heat the pre-vapor formulation, and a power supply configured to supply power to the heating element. The heating element includes a metal tube having a first end and a second end. The metal tube defines an opening therethrough. The metal tube includes a sidewall defining at least one spiral channel extending substantially continuously along a portion of the metal tube.

In at least one example embodiment, the spiral channel begins at a location about 0.5 mm to about 1.0 mm from at least one of the first end of the metal tube and the second end of the metal tube. The spiral channel ends at a location about 0.5 mm to about 1.0 mm from the first end of the metal tube.

In at least one example embodiment, the spiral channel includes about 2 to about 20 turns around the metal tube. Each turn is spaced from adjacent turns by about 0.05 mm to about 0.25 mm. Each turn is uniformly spaced from adjacent turns.

In at least one example embodiment, each turn is non-uniformly spaced from adjacent turns.

In at least one example embodiment, the spiral channel has a width ranging from about 0.1 mm to about 0.5 mm. The metal tube has a length ranging from about 3.0 mm to about 6.0 mm.

In at least one example embodiment, the spiral channel extends along about 2.0 mm to about 3.5 mm of the length of the metal tube. About 0.75 mm to about 2.0 mm of the length of the metal tube does not include the spiral channel.

The metal tube has an inner diameter ranging from about 0.1 mm to about 4.0 mm. The metal tube has a thickness ranging from about 0.05 mm to about 0.25 mm.

In at least one example embodiment, the electronic vaping device also includes a wick that extends through the opening in the metal tube, such that the metal tube surrounds at least a portion of the wick. A second portion of the wick extends into the reservoir.

In at least one example embodiment, the electronic vaping device also includes a wick that at least partially surrounds at least a portion of the metal tube.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly rioted. For purposes of clarity, various dimensions of the drawings may have been exaggerated.

FIG. 4 is a front view of a heating element according to at least one example embodiment.

DETAILED DESCRIPTION OF EXAMPLE EMBODIMENTS

Figure 1:
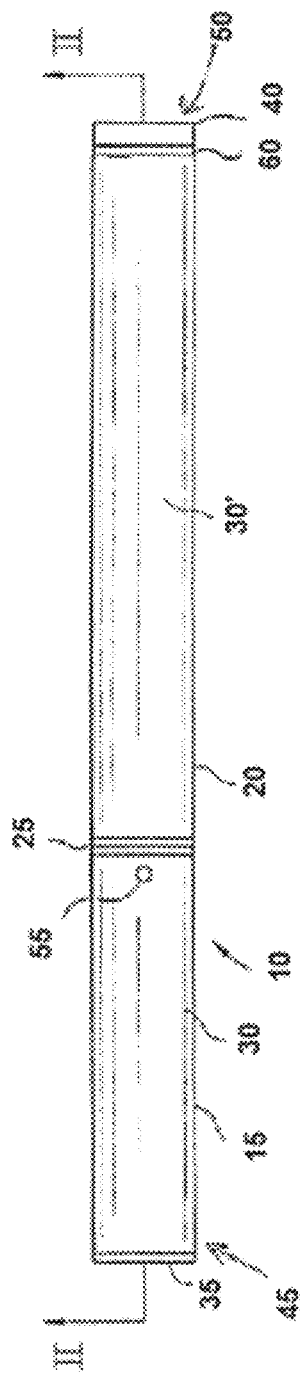
FIG. 1 is a side view of an electronic vaping device according to at least one example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

FIG. 1 is a side view of an e-vaping device according to at least one example embodiment.

In at least one example embodiment, as shown in FIG. 1, an electronic vaping device (e-vaping device) 10 may include a replaceable cartridge (or first section) 15 and a reusable battery section (or second section) 20, which may be coupled together at a threaded connector 25. It should be appreciated that the connector 25 may be any type of connector, such as a snug-fit, detent, clamp, bayonet, and/or clasp. An air inlet 55 extends through a portion of the connector 25.

In at least one example embodiment, the connector 25 may be the connector described in U.S. application Ser. No. 15/154,439, filed May 13, 2016, the entire contents of which is incorporated herein by reference thereto. As described in U.S. application Ser. No. 15/154,439, the connector 25 may be formed by a deep drawn process.

In at least one example embodiment, the first section 15 may include a first housing 30 and the second section 20 may include a second housing 30'. The e-vaping device 10 includes a mouth-end insert 35 at a first end 45.

In at least one example embodiment, the first housing 30 and the second housing 30' may have a generally cylindrical cross-section. In other example embodiments, the housings 30 and 30' may have a generally triangular cross-section along one or more of the first section 15 and the second section 20. Furthermore, the housings 30 and 30' may have the same or different cross-section shape, or the same or different size. As discussed herein, the housings 30, 30' may also be referred to as outer or main housings.

In at least one example embodiment, the e-vaping device 10 may include an end cap 40 at a second end 50 of the e-vaping device 10. The e-vaping device 10 also includes a light 60 between the end cap 40 and the first end 45 of the e-vaping device 10.

Figure 2:
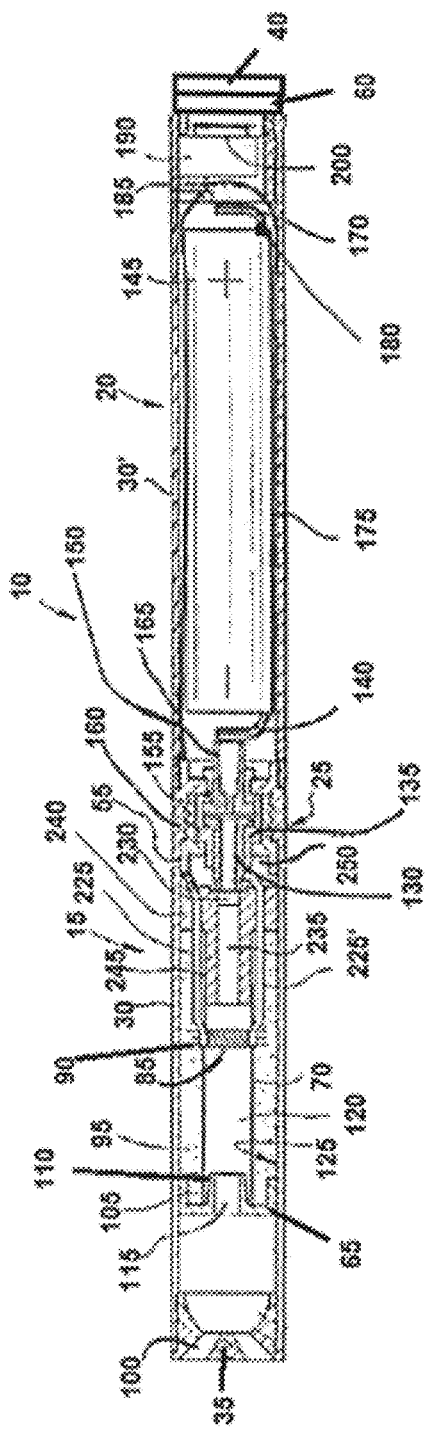
FIG. 2 is a cross-sectional view of the electronic vaping device of FIG. 1 along line according to at least one example embodiment.

FIG. 2 is a cross-sectional view along line II-II of the e-vaping device of FIG. 1.

In at least one example embodiment, as shown in FIG. 2, the first section 15 may include a reservoir 95 configured to store a pre-vapor formulation and a vaporizer 80 that may vaporize the pre-vapor formulation. The vaporizer 80 includes a heating element 85 and a wick 90. The wick 90 may draw the pre-vapor formulation from the reservoir 95. The e-vaping device 10 may include the features set forth in U.S. Patent Application Publication No. 2013/0192623 to Tucker et al. filed Jan. 31, 2013 and/or features set forth in U.S. patent application Ser. No. 15/135,930 to Holtz et al. filed Apr. 22, 2016, the entire contents of each of which are incorporated herein by reference thereto. In other example embodiments, the e-vaping device may include the features set forth in U.S. patent application Ser. No. 15/135,923 filed Apr. 22, 2016, and/or U.S. Pat. No. 9,289,014 issued Mar. 22, 2016, the entire contents of each of which is incorporated herein by this reference thereto.

In at least one example embodiment, the pre-vapor formulation is a material or combination of materials that may be transformed into a vapor. For example, the pre-vapor formulation may be a liquid, solid and/or gel formulation including, but not limited to, water, beads, solvents, active ingredients, ethanol, plant extracts, plant material (such as tobacco and/or non-tobacco plant material), natural or artificial flavors, and/or vapor formers such as glycerin and propylene glycol.

In at least one example embodiment, the first section 15 may include the housing 30 extending in a longitudinal direction and an inner tube (or chimney) 70 coaxially positioned within the housing 30.

In at least one example embodiment, a first connector piece 155 may include a male threaded section for effecting the connection between the first section 15 and the second section 20.

At an upstream end portion of the inner tube 70, a nose portion 245 of a gasket (or seal) 240 may be fitted into the inner tube 70; and an outer perimeter of the gasket 240 may provide a seal with an interior surface of the housing 30. The gasket 240 may also include a central, longitudinal air passage 235 in fluid communication with the inner tube 70 to define an inner passage (also referred to as a central channel or central inner passage) 120. A transverse channel 230 at a backside portion of the gasket 240 may intersect and communicate with the air passage 235 of the gasket 240. This transverse channel 230 assures communication between the air passage 235 and a space 250 defined between the gasket 240 and the first connector piece 155.

In at least one example embodiment, the first connector piece 155 may include a male threaded section for effecting the connection between the first section 15 and the second section 20.

In at least one example embodiment, at least two air inlets 55 may be included in the housing 30. Alternatively, a single air inlet 55 may be included in the housing 30. Such arrangement allows for placement of the air inlet 55 close to the connector 25 without occlusion by the presence of the first connector piece 155. This arrangement may also reinforce the area of air inlets 55 to facilitate precise drilling of the air inlets 55.

In at least one example embodiment, the air inlets 55 may be provided in the connector 25 instead of in the housing 30. In other example embodiments, the connector 25 may not include threaded portions.

In at least one example embodiment, the at least one air inlet 55 may be formed in the housing 30, adjacent the connector 25 to minimize the chance of an adult vaper's fingers occluding one of the ports and to control the resistance-to-draw (RTD) during wiping. In at least one example embodiment, the air inlet 55 may be machined into the housing 30 with precision tooling such that their diameters are closely controlled and replicated from one e-vaping device 10 to the next during manufacture.

In at least one example embodiment, the air inlets 55 may be sized and configured such that the e-vaping device 10 has a resistance-to-draw (RTD) in the range of from about 60 mm $H_2O$ to about 150 mm $H_2O$.

In at least one example embodiment, a nose portion 110 of a gasket 65 may be fitted into a first end portion 105 of the inner tube 70. An outer perimeter of the gasket 65 may provide a substantially tight seal with an interior surface 125 of the housing 30. The gasket 65 may include a central channel 115 disposed between the inner passage 120 of the inner tube 70 and the interior of the mouth-end insert 35, which may transport the vapor from the inner passage 120 to the mouth-end insert 35. The mouth-end insert 35 includes at least two outlets 100, which may be located off-axis from the longitudinal axis of the e-vaping device 10. The outlets 100 may be angled outwardly in relation to the longitudinal axis of the e-vaping device 10. The outlets 100 may be substantially uniformly distributed about the perimeter of the mouth-end insert 35 so as to substantially uniformly distribute vapor.

In at least one example embodiment, the space defined between the gasket 65, the gasket 240, the housing 30, and the inner tube 70 may establish the confines of the reservoir 95. The reservoir 95 may contain a pre-vapor formulation, and optionally a storage medium (not shown) configured to store the pre-vapor formulation therein. The storage medium may include a winding of cotton gauze or other fibrous material about the inner tube 70.

In at least one example embodiment, the reservoir 95 may at least partially surround the inner passage 120. The heating element 85 may extend transversely across the inner passage 120 between opposing portions of the reservoir 95. In some example embodiments, the heating element 85 may extend parallel to a longitudinal axis of the inner passage 120.

In at least one example embodiment, the reservoir 95 may be sized and configured to hold enough pre-vapor formulation such that the e-vaping device 10 may be configured for vaping for at least about 200 seconds. Moreover, the e-vaping device 10 may be configured to allow each puff to last a maximum of about 5 seconds.

In at least one example embodiment, the storage medium may be a fibrous material including at least one of cotton, polyethylene, polyester, rayon and combinations thereof. The fibers may have a diameter ranging in size from about 6 microns to about 15 microns (e.g., about 8 microns to about 12 microns or about 9 microns to about 11 microns). The storage medium may be a sintered, porous or foamed material. Also, the fibers may be sized to be irrespirable and may have a cross-section which has a Y-shape, cross shape, clover shape or any other suitable shape. In at least one example embodiment, the reservoir 95 may include a filled tank lacking any storage medium and containing only pre-vapor formulation.

During vaping, pre-vapor formulation may be transferred from the reservoir 95 and/or storage medium to the proximity of the heating element 85 via capillary action of the wick 90. The wick 90 may include at least a first end portion and a second end portion, which may extend into opposite sides of the reservoir 95. The heating element 85 may at least partially surround a central portion of the wick 90 such that when the heating element 85 is activated, the pre-vapor formulation in the central portion of the wick 90 may be vaporized by the heating element 85 to form a vapor.

In at least one example embodiment, the wick 90 may include filaments (or threads) having a capacity to draw the pre-vapor formulation. For example, the wick 90 may be a bundle of glass (or ceramic) filaments, a bundle including a group of windings of glass filaments, etc., all of which arrangements may be capable of drawing pre-vapor formulation via capillary action by interstitial spacings between the filaments. The filaments may be generally aligned in a direction perpendicular (transverse) to the longitudinal direction of the e-vaping device 10. In at least one example embodiment, the wick 90 may include one to eight filament strands, each strand comprising a plurality of glass filaments twisted together. The end portions of the wick 90 may be flexible and foldable into the confines of the reservoir 95. The filaments may have a cross-section that is generally cross-shaped, clover-shaped, Y-shaped, or in any other suitable shape.

In at least one example embodiment, the wick 90 may include any suitable material or combination of materials. Examples of suitable materials may be, but not limited to, glass, ceramic- or graphite-based materials. The wick 90 may have any suitable capillarity drawing action to accommodate pre-vapor formulations having different physical properties such as density, viscosity, surface tension and vapor pressure. The wick 90 may be non-conductive.

In at least one example embodiment, the heating element 85 may include a metal tube or cylinder including a side all.

The heating element 85 may extend fully or partially along the length of the wick 90. In some example embodiments, the heating element 85 may or may not be in contact with the wick 90.

The inner tube 70 may include a pair of opposing slots, such that the wick 90 and the first and second electrical leads 225, 225' or ends of the heating element 85 may extend out from the respective opposing slots. The provision of the opposing slots in the inner tube 70 may facilitate placement of the heating element 85 and wick 90 into position within the inner tube 70 without impacting edges of the slots. In at least one example embodiment, the inner tube 70 may have a diameter of about 4 mm and each of the opposing slots may have major and minor dimensions of about 2 mm by about 4 mm.

In at least one example embodiment, the first lead 225 is physically and electrically connected to the male threaded connector piece 155. As shown, the male threaded first connector piece 155 is a hollow cylinder with male threads on a portion of the outer lateral surface. The connector piece is conductive, and may be formed or coated with a conductive material. The second lead 225' is physically and electrically connected to a first conductive post 130. The first conductive post 130 may be formed of a conductive material (e.g., stainless steel, copper, etc.), and may have a T-shaped cross-section as shown in FIG. 2. The first conductive post 130 nests within the hollow portion of the first connector piece 155, and is electrically insulated from the first connector piece 155 by an insulating shell 135. The first conductive post 130 may be hollow as shown, and the hollow portion may be in fluid communication with the air passage 120. Accordingly, the first connector piece 155 and the first conductive post 130 form respective external electrical connections to the heating element 85.

In at least one example embodiment, the heating element 85 may heat pre-vapor formulation in the wick 90 by thermal conduction. Alternatively, heat from the heating element 85 may be conducted to the pre-vapor formulation by means of a heat conductive element or the heating element 85 may transfer heat to the incoming ambient air that is drawn through the e-vaping device 10 during vaping, which in turn heats the pre-vapor formulation by convection.

It should be appreciated that, instead of using a wick 90, the heating element 85 may include a porous material which incorporates a resistance heating element formed of a material having a high electrical resistance capable of generating heat quickly.

As shown in FIG. 2, the second section 20 includes a power supply 145, a control circuit 185, and a sensor 190. As shown, the control circuit 185 and the sensor 190 are disposed in the housing 30'. A female threaded second connector piece 160 forms a second end. As shown, the second connector piece 160 has a hollow cylinder shape with threading on an inner lateral surface. The inner diameter of the second connector piece 160 matches that of the outer diameter of the first connector piece 155 such that the two connector pieces 155, 160 may be threaded together to form the connector 25. Furthermore, the second connector piece 160, or at least the other lateral surface is conductive, for example, formed of or including a conductive material. As such, an electrical and physical connection occurs between the first and second connector pieces 155, 160 when connected.

As shown, a first lead 165 electrically connects the second connector piece 160 to the control circuit 185. A second lead 170 electrically connects the control circuit 185 to a first terminal 180 of the power supply 145. A third lead 175 electrically connects a second terminal 140 of the power supply 145 to the power terminal of the control circuit 185 to provide power to the control circuit 185. The second terminal 140 of the power supply 145 is also physically and electrically connected to a second conductive post 150. The second conductive post 150 may be formed of a conductive material (e.g., stainless steel, copper, etc.), and may have a T-shaped cross-section as shown in. FIG. 2. The second conductive post 150 nests within the hollow portion of the second connector piece 160, and is electrically insulated from the second connector piece 160 by a second insulating shell 215. The second conductive post 150 may also be hollow as shown. When the first and second connector pieces 155, 160 are mated, the second conductive post 150 physically and electrically connects to the first conductive post 130. Also, the hollow portion of the second conductive post 150 may be in fluid communication with the hollow portion of the first conductive post 130.

While the first section 15 has been shown and described as having the male connector piece and the second section 20 has been shown and described as having the female connector piece, an alternative embodiment includes the opposite where the first section 15 has the female connector piece and the second section 20 has the male connector piece.

In at least one example embodiment, the power supply 145 includes a battery arranged in the e-vaping device 10. The power supply 145 may be a Lithium-ion battery or one of its variants, for example a Lithium-ion polymer battery. Alternatively, the power supply 145 may be a nickel-metal hydride battery, a nickel cadmium battery, a lithium-manganese battery, a lithium-cobalt battery or a fuel cell. The e-vaping device 10 may be vapable by an adult vaper until the energy in the power supply 145 is depleted or in the case of lithium polymer battery, a minimum voltage cut-off level is achieved.

In at least one example embodiment, the power supply 145 is rechargeable. The second section 20 may include circuitry configured to allow the battery to be chargeable by an external charging device. To recharge the e-vaping device 10, an USB charger or other suitable charger assembly may be used as described below.

In at least one example embodiment, the sensor 190 is configured to generate an output indicative of a magnitude and direction of airflow in the e-vaping device 10. The control circuit 185 receives the output of the sensor 190, and determines if (1) the direction of the airflow indicates a draw on the mouth-end insert 8 (versus blowing) and (2) the magnitude of the draw exceeds a threshold level. If these vaping conditions are met, the control circuit 185 electrically connects the power supply 145 to the heating element 85; thus, activating the heating element 85. Namely, the control circuit 185 electrically connects the first and second leads 165, 170 (e.g., by activating a heating element power control transistor forming part of the control circuit 185) such that the heating element 85 becomes electrically connected to the power supply 145. In an alternative embodiment, the sensor 190 may indicate a pressure drop, and the control circuit 185 activates the heating element 85 in response thereto.

In at least one example embodiment, the control circuit 185 may also include a light 60, which the control circuit 185 activates to glow when the heating element 85 is activated and/or the battery 145 is recharged. The light 60 may include one or more light-emitting diodes (LEDs). The LEDs may include one or more colors (e.g., white, yellow, red, green, blue, etc.). Moreover, the light 60 may be arranged to be visible to an adult vaper during vaping, and may be positioned between the first end 45 and the second end 50 of the e-vaping device 10. In addition, the light 60 may be utilized for e-vaping system diagnostics or to indicate that recharging is in progress. The light 60 may also be configured such that the adult vaper may activate and/or deactivate the heating element activation light 60 for privacy.

In at least one example embodiment, the control circuit 185 may include a time-period limiter. In another example embodiment, the control circuit 185 may include a manually operable switch for an adult vaper to initiate heating. The time-period of the electric current supply to the heating element 85 may be set or pre-set depending on the amount of pre-vapor formulation desired to be vaporized.

Next, operation of the e-vaping device to create a vapor will be described. For example, air is drawn primarily into the first section 15 through the at least one air inlet 55 in response to a draw on the mouth-end insert 35. The air passes through the air inlet 55, into the space 250, through the transverse channel 230 into the air passage 235, into the inner passage 120, and through the outlet 100 of the mouth-end insert 35. If the control circuit 185 detects the vaping conditions discussed above, the control circuit 185 initiates power supply to the heating element 85, such that the heating element 85 heats pre-vapor formulation in the wick 90. The vapor and air flowing through the inner passage 120 combine and exit the e-vaping device 10 via the outlet 100 of the mouth-end insert 35.

When activated, the heating element 85 may heat a portion of the wick 90 for less than about 10 seconds.

In at least one example embodiment, the first section 15 may be replaceable. In other words, once the pre-vapor formulation of the cartridge is depleted, only the first section 15 may be replaced. An alternate arrangement may include an example embodiment where the entire e-vaping device 10 may be disposed once the reservoir 95 is depleted. In at least one example embodiment, the e-vaping device 10 may be a one-piece e-vaping device.

In at least one example embodiment, the e-vaping device 10 may be about 80 mm to about 110 mm long and about 7 mm to about 8 mm in diameter. For example, in one example embodiment, the e-vaping device 10 may be about 84 mm long and may have a diameter of about 7.8 mm.

Figure 3:
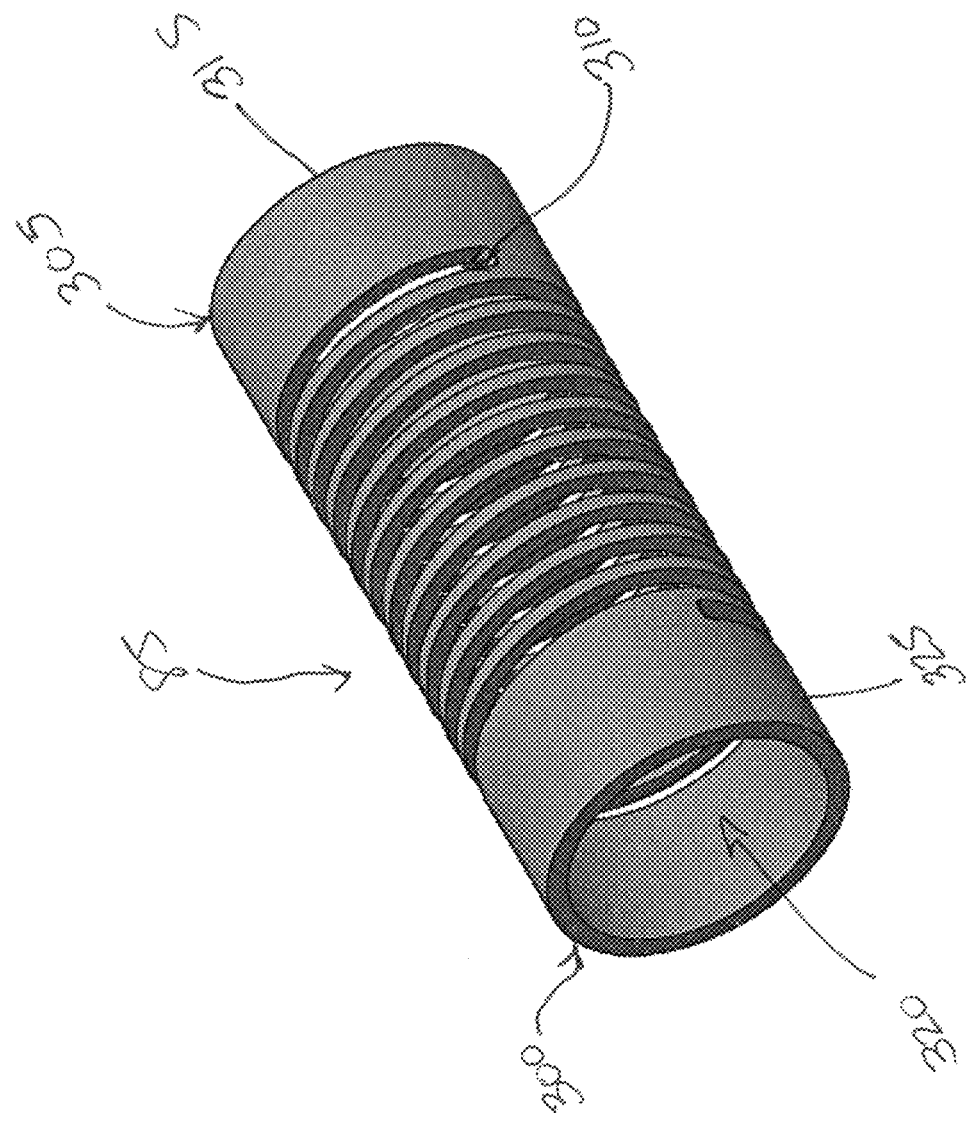
FIG. 3 is a perspective view of a heating element according to at least one example embodiment.

FIG. 3 is a perspective view of a heating element according to at least one example embodiment.

In at least one example embodiment, as shown in FIG. 3, the heating element 85 has a first end 300 and a second end 305. As discussed above, the heating element 85 is formed from a metal tube or hollow cylinder 315 having an opening 320 extending through the tube 315 from the first end 300 to the second end 305. The metal tube 315 includes a side wall 325. At least one channel 310 is laser etched and/or cut through the side wall 325. The channel 310 may be a spiral channel that circumscribes the metal tube 315 one or more times.

In at least one example embodiment, the heating element 85 may be formed of any suitable electrically resistive materials. Examples of suitable electrically resistive materials may include, but not limited to, copper, titanium, zirconium, tantalum and metals from the platinum group. Examples of suitable metal alloys include, but not limited to, stainless steel, nickel, cobalt, chromium, aluminum-titanium-zirconium, hafnium, niobium, molybdenum, tantalum, tungsten, tin, gallium, manganese and iron-containing alloys, and super-alloys based on nickel, iron, cobalt, stainless steel. For example, the heating element 85 may be formed of nickel aluminide, a material with a layer of alumina on the surface, iron aluminide and other composite materials, the electrically resistive material may optionally be embedded in, encapsulated or coated with an insulating material or vice-versa, depending on the kinetics of energy transfer and the external physicochemical properties required. The heating element 85 may include at least one material selected from the group consisting of stainless steel, copper, copper alloys, nickel-chromium alloys, super alloys and combinations thereof. In an example embodiment, the heating element 85 may be formed of nickel-chromium alloys or iron-chromium alloys. In another example embodiment, the heating element 85 may be a ceramic heating element having an electrically resistive layer on an outside surface thereof.

In at least one example embodiment, the at least one spiral channel 310 extends substantially continuously along a portion of a length of the metal tube 315. In other example embodiments, the spiral channel 310 does not extend continuously along the entire length of the metal tube 315. For example, the metal tube may include multiple spiral channels 310 (not shown) each extending only partially along the length of the metal tube 315.

In at least one example embodiment, the spiral channel 310 includes multiple turns about the circumference of the metal tube 315. Each turn extends a full 360° about the metal tube 315. In other example embodiments, the spiral channel 310 may include partial turns that do not fully circumscribe the metal tube 315.

In at least one example embodiment, each turn is uniformly spaced from adjacent turns. In some example embodiments, each turn is non-uniformly spaced from adjacent turns.

In at least one example embodiment, the heating element has a resistance ranging from about 2.5 ohms to about 4.5 ohms (e.g., about 3.0 ohms to about 4.0 ohms or about 3.25 ohms to about 3.75 ohms).

In at least one example embodiment, the metal tube is formed of at least one of stainless steel and Nichrome.

FIG. 4 is a front view of a heating element according to at least one example embodiment.

In at least one example embodiment, the spiral channel 310 has a width W1 ranging from about 0.1 mm to about 0.5 mm (e.g., about 0.2 mm to about 0.4 mm or about 0.25 mm to about 0.35 mm). The metal tube 315 has a length L1 ranging from about 3.0 mm to about 10.0 mm (e.g., about 4.0 mm to about 9.0 mm, about 5.0 mm to about 8.0 mm, or about 6.0 mm to about 7.0 mm).

In at least one example embodiment, the spiral channel 310 extends along about 2.0 mm to about 3.5 mm (e.g., about 2.5 m to about 3.0 mm, or about 2.75 mm) of the length L1 of the metal tube 315. About 0.75 mm to about 2.0 mm (e.g., about 1.0 mm to about 1.5 mm) of the length L1 of the metal tube 315 does not include spiral channel 310. Thus, only a portion of the metal tube 315 includes the spiral channel 310.

In at least one example embodiment, the spiral channel 310 begins at a location about 0.5 mm to about 1.0 mm from at least one of the first end 300 of the metal tube 315 and the second end 305 of the metal tube 315.

In at least one example embodiment, the spiral channel 310 ends at a location about 0.5 mm to about 1.0 mm from at least one of the first end 300 of the metal tube 315 and the second end 305 of the metal tube 315.

The spiral channel 310 may be closer to one end of the metal tube 315 than the other or the spiral channel 310 may be a same distance from the first end 300 and the second end 305 of the metal tube 315.

In at least one example embodiment, the spiral channel 310 includes about 2 to about 20 (e.g. about 4 to about 18, about 6 to about 16, or about 10 to about 14) turns around the circumference of the metal tube 315. Each turn is spaced from adjacent turns by a width W2 of about 0.05 mm to about 0.25 mm (e.g., about 0.1 mm to about 0.2 mm). Stated another way, the thickness of the spiral channel 310 ranges from about 0.05 mm to about 0.25 mm (e.g., about 0.1 mm to about 0.2 mm).

In at least one example embodiment, the metal tube 315 has a longitudinally extending axis x. Each turn may be angled with respect to the axis x by about 5° to about 90° (e.g., about 10° to about 85°, about 15° to about 80°, about 20° to about 75°, about 25° to about 70°, about 30° to about 65°, about 35° to about 60°, about 40° to about 55°, or about 45° to about 50°).

Figure 5:
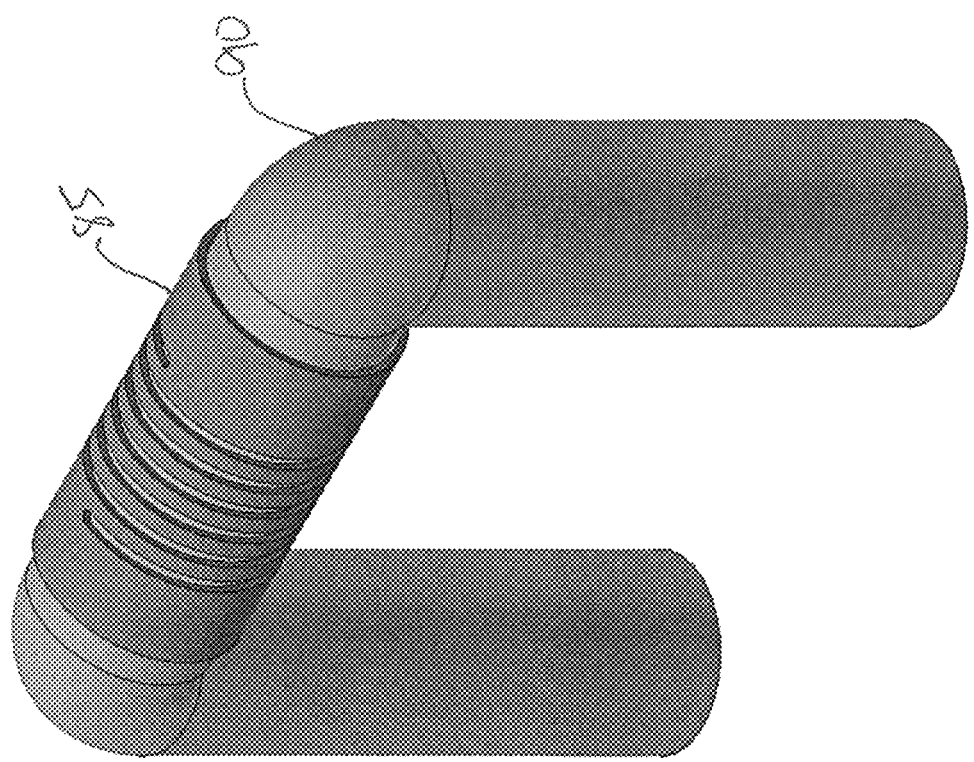
FIG. 5 is a perspective view of a heating element assembly according to at least one example embodiment.

FIG. 5 is a perspective view of a heating element assembly according to at least one example embodiment.

In at least one example embodiment, the heating element 85 is the same as in FIGS. 2-4 except that the wick 90 is generally U-shaped.

Figure 6:
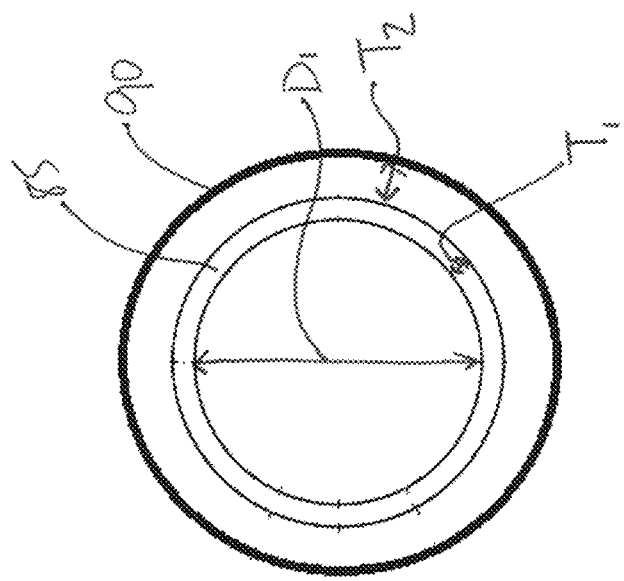
FIG. 6 is an end view of a heating element assembly according to at least one example embodiment.

FIG. 6 is an end view of a heating element assembly according to at least one example embodiment.

In at least one example embodiment, the heating element 85 is the same as in FIGS. 2-5 except that the wick 90 surrounds the heating element 85. The wick 90 may be a tube of wicking material or a wicking material that is wrapped around at least a portion of the heating element 85.

In at least one example embodiment, the metal tube 315 has an inner diameter D1 ranging from about 0.1 mm to about 4.0 mm (e.g. about 0.5 mm to about 3.5 mm, about 1.0 mm to about 3.0 mm, or about 1.5 mm to about 2.5 mm). The metal tube has a thickness T1 ranging from about 0.05 mm to about 0.25 mm (e.g. about 0.1 mm to about 0.2 mm).

The heating assembly of FIG. 6 may be used with a cartridge or electronic vaping device described in U.S. application Ser. No. 15/224,866, filed Aug. 1, 2016 or U.S. application Ser. No. 15/135,930, filed Apr. 22, 2016, the entire contents of each of which are incorporated herein by reference.

Example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

We claim:

1. A cartridge of an electronic vaping device comprising:
   a reservoir configured to store a pre-vapor formulation;
   a heating element configured to heat the pre-vapor formulation, the heating element including,
      a metal tube having a first end and a second end, the metal tube defining an opening therethrough, the metal tube including,
         a sidewall defining at least one spiral channel extending substantially continuously along at least a portion of the metal tube, the spiral channel having a uniform width along a length of the spiral channel, a thickness of the spiral channel ranging from 0.1 mm to 0.2 mm, and the spiral channel including 10 to 14 turns around a circumference of the metal tube, each turn being angled about 35° to 60° with respect to a longitudinal axis of the metal tube; and
   a wick extending through the opening in the metal tube, such that the metal tube surrounds a portion of the wick.

2. The cartridge of claim 1, wherein the spiral channel begins at a location about 0.5 mm to about 1.0 mm from the first end of the metal tube.

3. The cartridge of claim 1, wherein the spiral channel ends at a location about 0.5 mm to about 1.0 mm from the first end of the metal tube, the second end of the metal tube, or both the first end of the metal tube and the second end of the metal tube.

4. The cartridge of claim 1, wherein each turn is spaced from adjacent turns by about 0.05 mm to about 0.5 mm.

5. The cartridge of claim 1, wherein each turn is uniformly spaced from adjacent turns.

6. The cartridge of claim 1, wherein each turn is non-uniformly spaced from adjacent turns.

7. The cartridge of claim 1, wherein the metal tube has a length ranging from about 3.0 mm to about 6.0 mm.

8. The cartridge of claim 1, wherein the spiral channel extends along about 2.0 mm to about 3.5 mm of a length of the metal tube, and about 0.75 mm to about 2.0 mm of the length of the metal tube does not include the spiral channel.

9. The cartridge of claim 1, wherein the metal tube has an inner diameter ranging from about 0.1 mm to about 4.0 mm.

10. The cartridge of claim 1, wherein the metal tube has a thickness ranging from about 0.05 mm to about 0.25 mm.

11. The cartridge of claim 1, wherein the heating element has a resistance ranging from about 2.5 ohms to about 4.5 ohms.

12. The cartridge of claim 1, wherein the metal tube includes stainless steel, Nichrome, or both stainless steel and Nichrome.

13. An electronic vaping device comprising:
a reservoir configured to store a pre-vapor formulation;
a heating element configured to heat the pre-vapor formulation, the heating element including,
- a metal tube having a first end and a second end, the metal tube defining an opening therethrough, the metal tube including,
- a sidewall defining at least one spiral channel extending substantially continuously along at least a portion of the metal tube, the spiral channel having a uniform width along a length of the spiral channel, a width of the spiral channel ranging from 0.1 mm to 0.2 mm, and the spiral channel including 10 to 14 turns around a circumference of the metal tube, each turn being angled about 35° to 60° with respect to a longitudinal axis of the metal tube;
a wick extending through the opening in the metal tube, such that the metal tube surrounds a portion of the wick; and
a power supply configured to supply power to the heating element.

14. The electronic vaping device of claim 13, wherein the spiral channel begins at a location about 0.5 mm to about 1.0 mm from the first end of the metal tube, the second end of the metal tube, or both the first end of the metal tube and the second end of the metal tube.

15. The electronic vaping device of claim 13, wherein the spiral channel ends at a location about 0.5 mm to about 1.0 mm from the first end of the metal tube.

16. The electronic vaping device of claim 13, wherein each turn is uniformly spaced from adjacent turns.

17. The electronic vaping device of claim 13, wherein each turn is non-uniformly spaced from adjacent turns.

18. The electronic vaping device of claim 13, wherein the metal tube has a length ranging from about 3.0 mm to about 6.0 mm.

19. The electronic vaping device of claim 13, wherein the spiral channel extends along about 2.0 mm to about 3.5 mm of the length of the metal tube, and about 0.75 mm to about 2.0 mm of the length of the metal tube does not include the spiral channel.

20. The electronic vaping device of claim 13, wherein the metal tube has an inner diameter ranging from about 0.1 mm to about 4.0 mm and the metal tube has a thickness ranging from about 0.05 mm to about 0.25 mm.

\* \* \* \* \*